United States Patent [19]

Dicoi et al.

[11] 4,107,160

[45] Aug. 15, 1978

[54] CONTINUOUS PROCESS FOR THE RECOVERY OF CAPROLACTAM

[75] Inventors: Ovidiu Dicoi, Offenbach; Erwin Doerr, Markt Schwaben, both of Fed. Rep. of Germany

[73] Assignee: Zimmer Aktiengesellschaft, Frankfurt, Fed. Rep. of Germany

[21] Appl. No.: 827,370

[22] Filed: Aug. 24, 1977

[51] Int. Cl.² .............................................. C07D 201/12
[52] U.S. Cl. ................................. 260/239.3 A; 23/263
[58] Field of Search ................................ 260/239.3 A

[56] References Cited

U.S. PATENT DOCUMENTS

| | | | |
|---|---|---|---|
| 2,667,483 | 1/1954 | Zeegers ......................... | 260/239.3 A |
| 2,930,790 | 3/1960 | Weise et al. ................... | 260/239.3 A |
| 2,952,675 | 9/1960 | Bolle ............................. | 260/239.3 A |
| 2,960,499 | 11/1960 | Boon ............................. | 260/239.3 A |
| 3,459,640 | 8/1969 | Tsunawki et al. ............. | 260/239.3 A |

*Primary Examiner*—Natalie Trousop
*Assistant Examiner*—Robert T. Bond
*Attorney, Agent, or Firm*—Allegretti, Newitt, Witcoff & McAndrews

[57] ABSTRACT

A process for the continuous recovery of caprolactam from either solid polycaprolactam waste by depolymerization or from liquid polycaprolactam extraction water from an extraction zone where, in either instance, a caprolactam water vapor mixture is produced and subsequently upgraded in a distillation zone to provide a dilute mixture of caprolactam and water vapor. A minor portion of this dilute caprolactam water vapor is condensed and recycled to the distillation zone. The remaining, major portion of this mixture is compressed and admixed with fresh steam, superheated and passed to either the extraction zone or depolymerization reaction.

2 Claims, 3 Drawing Figures

CONTINUOUS PROCESS FOR THE RECOVERY OF CAPROLACTAM

BACKGROUND OF THE INVENTION

The invention relates to an apparatus and a continuous process for the recovery of caprolactam from solid polycaprolactam waste and/or polycaprolactam extraction water.

Large quantities of solid polycaprolactam waste accumulate during the processing of polycaprolactam to produce, for example, fibers filaments, brittles, fabrics, and castings. Furthermore, the polycondensation of caprolactam results not only in the production of polycaprolactam but also in the production of low-molecular weight lactam oligomers in the residual monomer caprolactam. These low-molecular lactam oligomers are removed from the polymer by means of extraction with water, in which case the obtained extract contains about 75–80 percent monomers and 20–25 percent oligomers.

The process of depolymerizing the solid lactam, for example, in an autoclave by means of water vapor, and the process of reusing the caprolactam thus obtained after depolymerization is well known. The apparatus utilized for this prior art process consists of a depolymerization reactor wherein the solid polycaprolactam waste is depolymerized by means of superheated water vapor, i.e. steam, a upgrading or distillation column wherein the concentration of caprolactam in the caprolactam water mixture discharged from the depolymerization reactor is upgraded, and a further treatment apparatus wherein the caprolactam water solution discharged from upgrading column is subject to further treatment, for example, refining and distillation.

The process of evaporating the aqueous caprolactam oligomer solutions in evaporators such as multi-stage evaporators and the recovery of the monomer lactam from the remaining residue, for example, again by distillation, is also well known. In these two processes, very large amounts of superheated water vapor are required to depolymerize the solid waste and to evaporate the water solutions. The energy required to evaporate the water solutions is also supplied by passing water vapor into the apparatus. Present practice requires fresh superheated steam to be constantly passed to the depolymerization reactor and evaporator, respectively, while the water vapor remaining after the completion of the concentration of the caprolactam water vapor mixture, which still contains very minute amounts of caprolactam, is removed from the treatment process and which is, after condensation, merely discharged as waste water. This requires continuous generation of fresh superheated water vapor and a high energy input. Moreover, the discharge of waste water containing caprolactam into the environment is ecologically unacceptable.

SUMMARY OF THE INVENTION

The invention is based on the concept of recycling the water vapor accumulating in the concentration or distillation step for recovery of the caprolactam to the polycaprolactam depolymerization reactor and to the evaporator for the polycaprolactam extraction water, respectively.

According to the present invention, the remaining water vapor is recycled to a treatment process when the concentration of the caprolactam water vapor mixture has been upgraded. This treatment includes condensing a minor portion of the water vapor discharged from the upgrading step and refluxing it, as reflux condensate, to the upgrading step. The remaining major portion of the water vapor is compressed; the resultant compressed and heated water vapor is then mixed with fresh heating vapor, i.e. steam; and, the entire water vapor mixture superheated and recycled to the depolymerization and, evaporation step, respectively.

The process for depolymerizing solid polycaprolactam is characterized by utilizing the following additional apparatus after the depolymerization reactor: a condenser wherein a minor amount of the water vapor discharged from the upgrading column is condensed, a water vapor compressor wherein the majority of the water vapor discharged from the upgrading column is compressed, a mixing battery wherein the compressed water vapor discharged from the water vapor compressor is mixed with fresh heating vapor, i.e. steam, and a steam superheater wherein the combined water vapor is heated further and from which the heated water vapor is recycled to the depolymerization reactor.

The process for evaporating polycaprolactam extraction water is characterized by utilizing, in addition to the treatement apparatus, the following additional apparatus: a condenser wherein a minor amount of the water vapor discharged from the upgrading column is condensed, a water vapor compressor wherein the major portion of the water vapor discharged from the upgrading column is compressed, and a mixing battery wherein the water vapor discharged from the compressor is mixed with fresh heating steam before the water vapor is refluxed into the evaporator.

In addition to the treatment apparatus per se, a plant for the continuous recovery of caprolactam from solid polycaprolactam waste and polycaprolactam extraction water consists of the following additional apparatus: a condenser wherein a minor portion of the water vapor discharged from the upgrading column is condensed, a water vapor compressor wherein the major, remaining portion of the water vapor discharged from the upgrading column is compressed, mixing battery wherein the major portion of the compressed water vapor discharged from the water vapor compressor is mixed with fresh heating vapor, i.e. steam, whereupon the combined water vapor is refluxed into the evaporator, and a steam superheater wherein the minor portion of the compressed water vapor discharged from the water vapor compressor is heated further and from which the heated water vapor is refluxed to the depolymerization reactor.

The process according to the invention is preformed by condensing a minor portion of the water vapor discharged from the upgrading step and refluxing it to the upgrading step, separately compressing the remaining, large portion of the water vapor, admixing the compressed vapor with fresh heating vapor, i.e. steam, and then superheating and refluxing this mixture to the depolymerization stepand/or evaporation step.

Preferably about 20–10 percent by weight of the water vapor discharged from the upgrading step is condensed, while about 90–98 percent by weight of the discharged water vapor is compressed.

The process is performed by continously feeding ground, solid polycaprolactam waste into a depolymerization apparatus, and liquid polycaprolactam extraction water into an evaporator. At the same time, 85 percent aqueous orthophosphoric acid is continuously passed to the apparatus filled with solid polycaprolactam waste. On treating the products with superheated water vapor, the vapors containing water and caprolactam escape continuously from the treatment apparatus with a mean caprolactam content of about 80–90 percent by weight, while the oligomer bottoms, consisting of high-molecular linked polymers and organic phosphorus compounds, are removed discontinuously from the treatment vessels.

The escaping vapors are passed to an upgrading column where they are condensed. The water formed during condensation can then be removed by steam under normal or reduced pressure.

A minor portion of the thus formed water vapor is then condensed and recycled, as reflux condensate, to the upgrading column. The remaining greater portion of the water vapor is compressed in a water vapor compressor. This compressed water vapor is then mixed with fresh heating vapor, i.e. steam, and either refluxed immediately to the treatment apparatus or first passed through a steam heater, where it is heated further before being passed to the treatment apparatus.

DETAILED DESCRIPTION OF THE INVENTION

Examples illustrating the application of the invention are shown in FIGS. 1–3.

Figure 1:
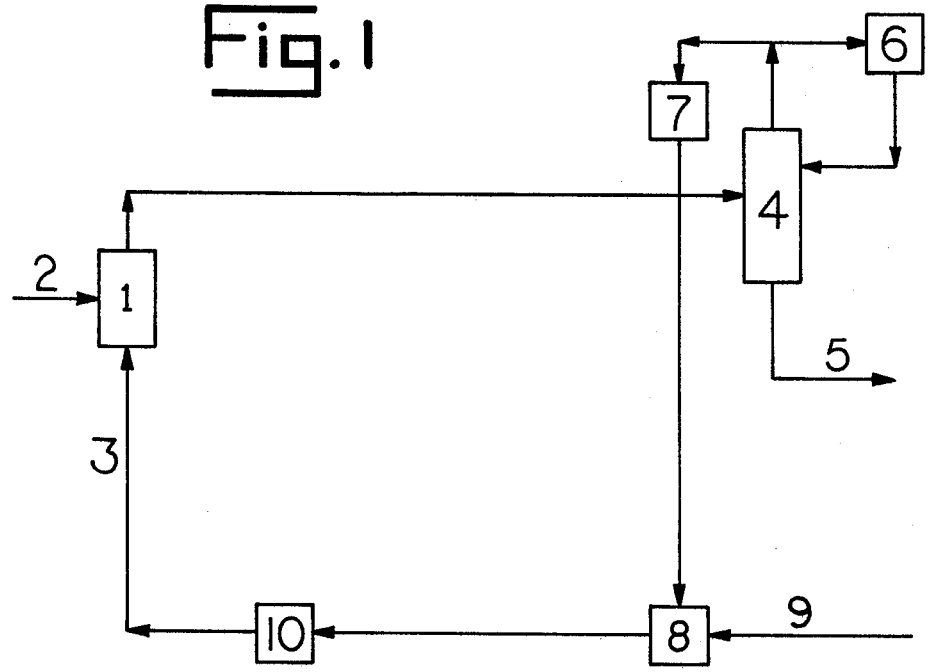
FIG. 1 depicts a plant for the continuous recovery of caprolactam from solid polycaprolactam waste.
Figure 2:
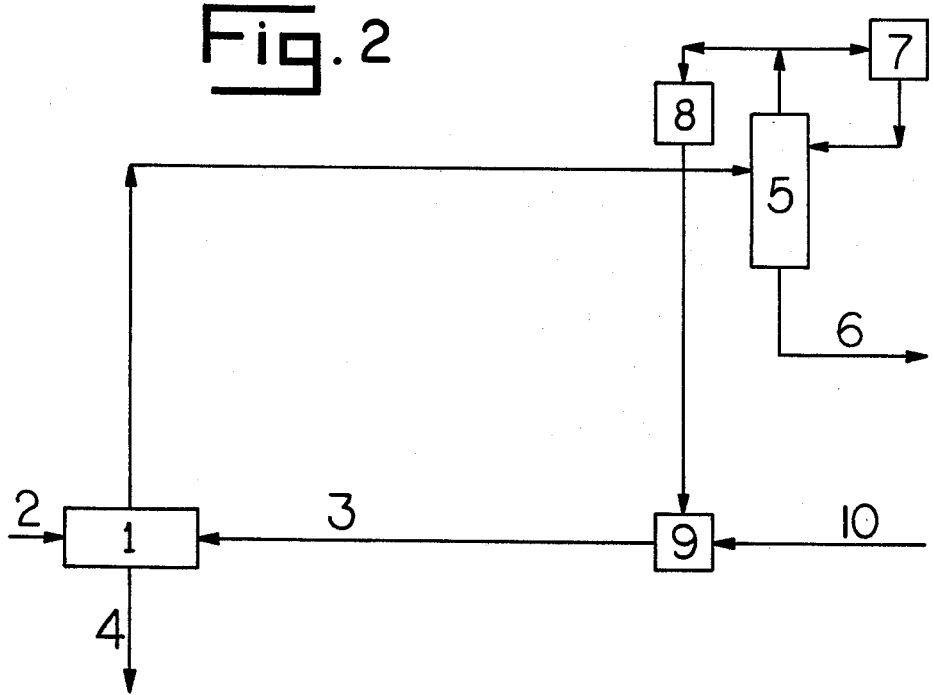
FIG. 2 shows a plant for the continuous recovery of caprolactam from liquid polycaprolactam extraction water.
Figure 3:
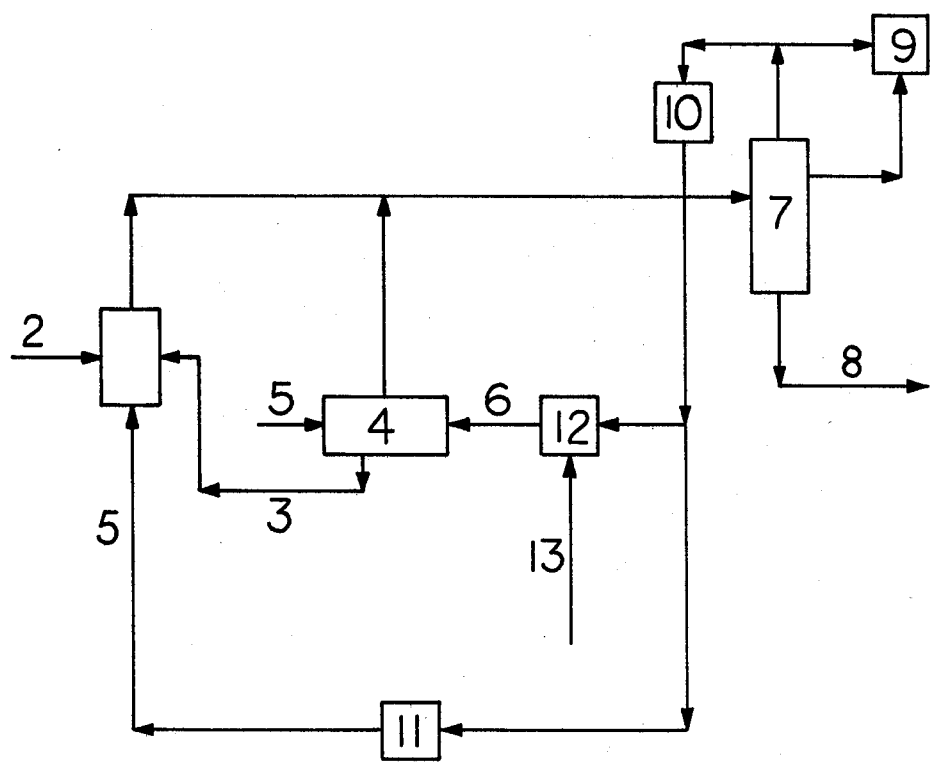
FIG. 3 illustrates a plant for the continuous recovery of caprolactam from solid polycaprolactam waste and liquid polycaprolactam extraction water.

The advantages gained by the invention can be attributed to the fact that the water vapor formed during upgrading is being recycled again and again to the polycaprolactam treatment cycle thus offering substantial savings in the energy costs associated with the generation of fresh heating vapor. Furthermore, the invention is environmentally acceptable since its implementation eliminates the discharging, into the environment, water vapor formed in the upgrading step which contains lactam.

EXAMPLE 1

A depolymerization reactor 1 was charged continuously via a pipeline, 2 with ground, solid polycaprolactam waste (nylon6) and polycaprolactam extraction water at a rate of 500 kg/h, superheated water vapor having a temperature of 340° C at a rate of 2,000 kg/h, and 12.8 liters of 85 per cent aqueous phosphoric acid. At the same time, a caprolactam water vapor mixture having a temperature of about 250° C and a pressure of 1.3 bar was discharged continuously at a rate of 2,485 kg/h from the depolymerization reactor and passed into an upgrading column 4. The caprolactam water mixture contained about 19.5 percent by weight caprolactam.

The concentration of caprolactam in the mixture was upgraded in upgrading column 4 at a temperature ranging between 120° C and 140° C and under a slight pressure of 1.1 bar. A yield of 545 kg/h of caprolactam water solution having a caprolactam content of about 90 percent by weight was discharged for further treatment from upgrading column 4 via a pipeline 5. Water vapor containing about 440 ppm caprolactam was discharged overhead from the upgrading column 4 at a temperature of 102° C and a pressure of 1.1 bar at a rate of approximately 1,940 kg/h. Approximately 2 percent by weight of this water vapor was refluxed, as reflux condensate, via condenser 6 to the upgrading column. The main stream of the water vapor was passed to a water vapor compressor 7 wherein the temperature of the water vapor was increased by 60° C and its pressure was increased by 1.6 bar.

Water vapor was discharged from water vapor compressor 7 at a temperature of about 170° C, a pressure of 2.7 bar and at a rate of 1,850 kg/h. The water vapor was then mixed in a mixing battery 8 with fresh heating vapor, i.e. steam, introduced via a pipeline 9 at a rate of 150 kg/h. The combined heating vapor was then passed to a steam superheater 10, heated to 340° C–370° C, and recycled via pipeline 3 to depolymerization reactor 1 for the purpose of depolymerizing the polycaprolactam waste.

EXAMPLE 2

Evaporator 1 was charged continuously via pipeline 2 with polycaprolactam extraction water containing about 10 percent by weight caprolactam at a rate of 1,700 kg/h. At the same time, superheated steam was passed via a pipeline 3 to evaporator 1 at a rate of 1,740 kg/h. A caprolactam water vapor mixture, containing 7 percent by weight of caprolactam, was produced at an operating temperature of 105° C and under a slight pressure of 1.15 bar at a rate of 1,658 kg/h and passed into upgrading column 5. The high-boiling components of the polycaprolactam extraction water was discharged continuously from the evaporator 1 via a pipeline 4 for the purpose of a subsequent separation of the oligomer. The concentration of the caprolactam water vapor mixture was then upgraded in the upgrading column 5 at temperatures between 102° C and 140° C and at a rate of 142 kg/h to produce a caprolactam water solution containing about 90 percent by weight of caprolactam. This caprolactam water solution was discharged via a pipeline 6 from the upgrading column 5 for further treatment.

Water vapor containing about 400 ppm caprolactam was discharged from the upgrading column 5 at a temperature of about 120° C and a pressure of 1.1 bar at a rate of approximately 1,520 kg/h. Approximately 2 percent by weight of this water vapor was refluxed, as reflux condensate, via a condenser 7 to the upgrading column 5. The main water vapor stream was passed to water vapor compressor 8 wherein the temperature of the water vapor was increased about 60° C, and its pressure was increased by 1.6 bar.

Water vapor was discharged from the evaporator compressor 8 at a temperature of 170° C and a pressure of 2.7 bar at a rate of 1,440 kg/h and this water vapor was mixed in a mixing battery 9, with fresh heating vapor, i.e. steam, introduced via the pipeline 10 at a rate of 300 kg/h. The entire water vapor mixture was then passed to evaporator 1 for evaporating the polycaprolactam extraction water.

EXAMPLE 3

A depolymerization reactor 1 was continuously charged with 200 kg/h ground solid polyamide waste (nylon 6) via pipeline 2, 62 kg/h oligomer bottoms from an evaporator 4 via a pipeline 3, 1,050 kg/h superheated water vapor at a temperature between 340° C and 370° C via a pipeline 5 and 6.7 liters of 85 percent aqueous orthophosphoric acid. At the same time, a caprolactam water vapor mixture was discharged from the depolymerization reactor 1 at a rate of 1,312 kg/h at a temperature of about 250° C and a pressure of 1.3 bar. This caprolactam water vapor mixture contained about 19.5 percent by weight caprolactam.

Evaporator 4 was also charged continuously via a pipeline 5 with a polycaprolactam extraction water having a caprolactam content of about 10 percent at a rate of 2,500 kg/h. At the same time, superheated water vapor was fed to the evaporator 4 via pipeline 6 at a rate of 2,780 kg/h. A caprolactam water vapor mixture having a caprolactam content of 7 percent by weight was produced in the evaporator 4 at a rate of 2,437 kg/h, a temperature of 105° C and a slight pressure of 1.15 bar. The polycaprolactam water vapor mixtures discharged from the depolymerization reactor 1 and evaporator 4 were combined and passed to upgrading column 7. The combined caprolactam water vapor mixture was concentrated in this apparatus at temperatures ranging between 102° C and 140° C and at a pressure of 1.1 bar to a solution containing about 90 percent by weight caprolactam.

This produced a caprolactam water solution at a rate of 357 kg/h, which was discharged via a pipeline 8 from the upgrading column 7 for further treatment.

Water vapor was discharged overhead from the upgrading column 7 at a temperature of about 102° C and a pressure of 1.1 bar at a rate of about 3,250 kg/h. The caprolactam content of this overhead solution was about 400 ppm. Water vapor in the amount of 2 percent by weight was refluxed, as reflux condensate, via a condenser 9 to the upgrading column 7. The main water vapor stream was passed into a water vapor compressor where the temperature of the water vapor was increased by about 60° C and the pressure was increased by 1.6 bar. Water vapor was discharged from compressor 10 at a temperature of 170° C and a pressure of 2.7 bar at a rate of 3,080 kg/h of which approximately one-third, i.e. 1,050 kg/h, were passed to a superheater 11 and recycled as superheated water vapor via pipeline 5 to the depolymerization reactor 1. Two-thirds of the water vapor discharged from the compressor 10, i.e. 2,030 kg/h, were mixed in a mixing battery 12 with fresh heating vapor at a rate of 550 kg/h, introduced via pipeline 13, and recycled to the evaporator 4 for evaporation of the polycaprolactam extraction water.

We claim as our invention:

1. A process for the continuous recovery of caprolactam from either solid polycaprolactam waste by a depolymerization reaction or from liquid polycaprolactam extraction water produced by a caprolactam extraction zone wherein, in either instance, a caprolactam water vapor mixture is produced and subsequently ungraded, in a distillation zone, to provide a concentrated caprolactam solution and a dilute, caprolactam water vapor overhead mixture which comprises condensing a minor portion of the caprolactam water vapor mixture;

recycling the resultant condensed mixture to the distillation zone;

compressing the remaining, major portion of the water vapor;

admixing the compressed vapor with fresh steam;

superheating the resultant compressed vapor, fresh steam mixture; and passing the superheated mixture to the caprolactam depolymerization reaction or caprolactam extraction zone.

2. A process according to claim 1 wherein the minor portion of the caprolactam water vapor mixture comprises 2–20 percent by weight of the overhead mixture and the major portion of the caprolactam water vapor mixture comprises 90–98 percent by weight of the overhead mixture.

* * * * *